US00PP20679P2

(12) United States Plant Patent
Fynewever

(10) Patent No.: US PP20,679 P2
(45) Date of Patent: Jan. 26, 2010

(54) ***VERONICA* PLANT NAMED 'FOXY LADY'**

(50) Latin Name: *Veronica spicata*
Varietal Denomination: Foxy Lady

(76) Inventor: Daniel R. Fynewever, 3824 - 47th St, Hamilton, MI (US) 49419

( * ) Notice: Subject to any disclaimer, the term of this patent is extended or adjusted under 35 U.S.C. 154(b) by 0 days.

(21) Appl. No.: 12/283,381

(22) Filed: Sep. 11, 2008

(51) Int. Cl.
*A01H 5/00* (2006.01)

(52) U.S. Cl. ..... Plt./251

(58) Field of Classification Search ..... Plt./251
See application file for complete search history.

*Primary Examiner*—Kent L Bell

(57) ABSTRACT

The new and distinct cultivar of ornamental Spiked Speedwell *Veronica spicata* 'Foxy Lady' with erect compact spikes of numerous two-tone ruby and white buds and flowers above low mats of foliage and suitable as a potted plant, for the garden, and for cut flower arrangements.

2 Drawing Sheets

Botanical classification: *Veronica spicata.*
Variety denomination: 'Foxy Lady'.

BACKGROUND OF THE INVENTION

The present invention relates to the new and distinct cultivar of Spiked Speedwell, botanically known as *Veronica spicata* 'Foxy Lady', and hereinafter referred to as the cultivar 'Foxy Lady' or the "plant". The new plant was discovered in the summer of 2005 by Daniel R. Fynewever in the production fields of a nursery in Hamilton, Mich., USA, as a whole plant non-induced sport of *Veronica spicata* 'Red Fox' (not patented). The plant has been asexually propagated by stem cuttings and tissue culture at the same nursery in the greenhouses in Zeeland, Mich., and subsequent asexually propagated plants found to be identical to the original selection.

BRIEF SUMMARY OF THE PLANT

*Veronica spicata* 'Foxy Lady' is unique from all other Spiked Speedwell known to the inventor. Other forms have white, lavender, blue or pinkish lavender flowers, but this is the only variety known by the applicant to have two-tone ruby and white flowers. The closest comparison variety is *Veronica* 'Red Fox', which has a solid pinkish lavender flower.

The following are traits of *Veronica spicata* 'Foxy Lady' that in combination distinguish it from all other known Spiked Speedwell:

1. Stiff; upright, compact spikes above short mats of foliage.
2. Numerous compact flowers of distinctly two-toned colors with white on the petal margins and ruby in the central portion of the petals.
3. Buds starting off white to light pink and becoming two-toned buds of white and ruby.

BRIEF DESCRIPTION OF THE DRAWINGS

The photographs of the new plant demonstrate the unique traits of 'Foxy Lady' and the overall appearance of the plant. The colors are as accurate as reasonably possible with color reproductions. Variation in ambient light spectrum, source and direction may cause the appearance of minor variation in color.

DETAILED BOTANICAL DESCRIPTION

Figure 1:
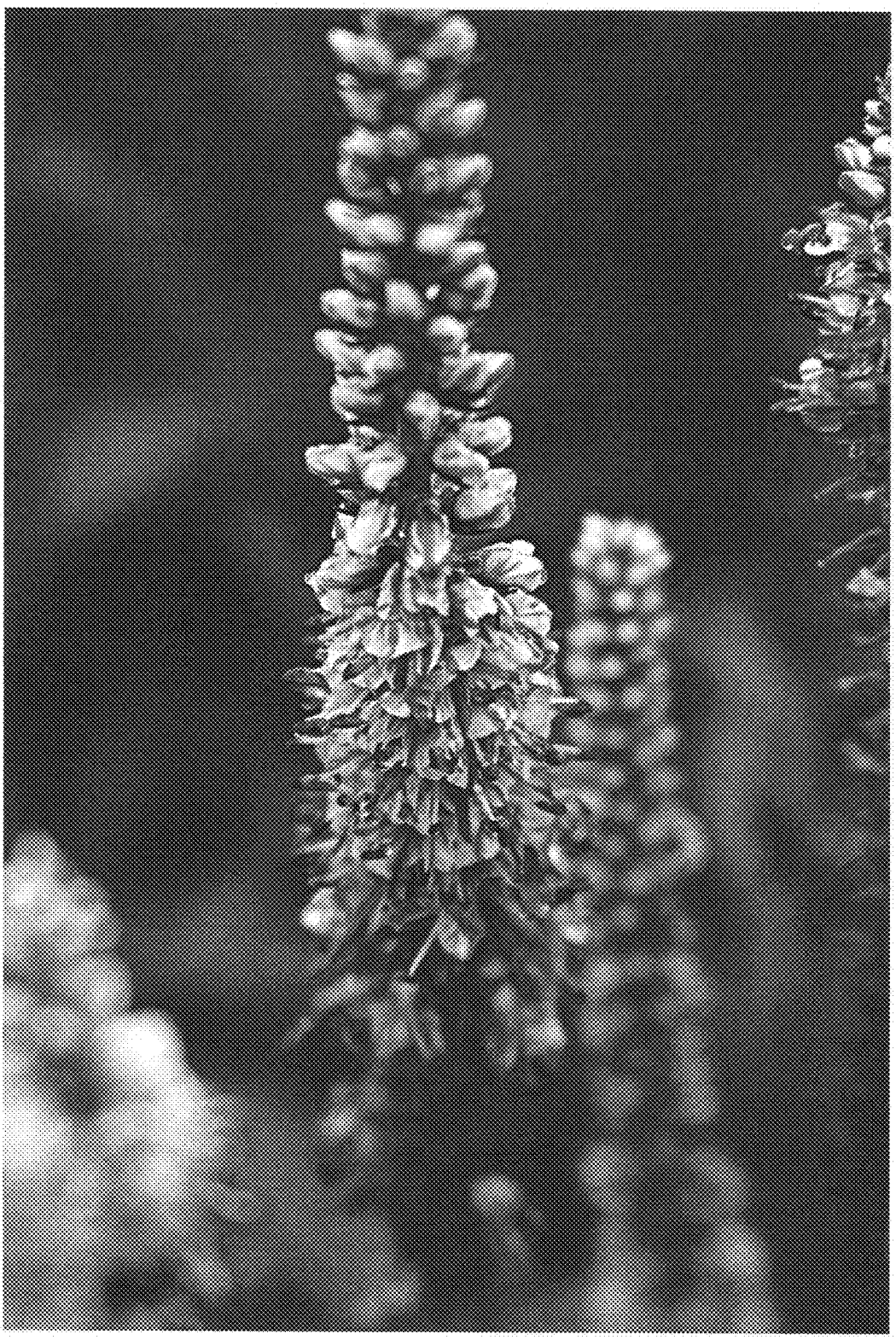
FIG. 1 shows a close-up of the flower.
Figure 2:
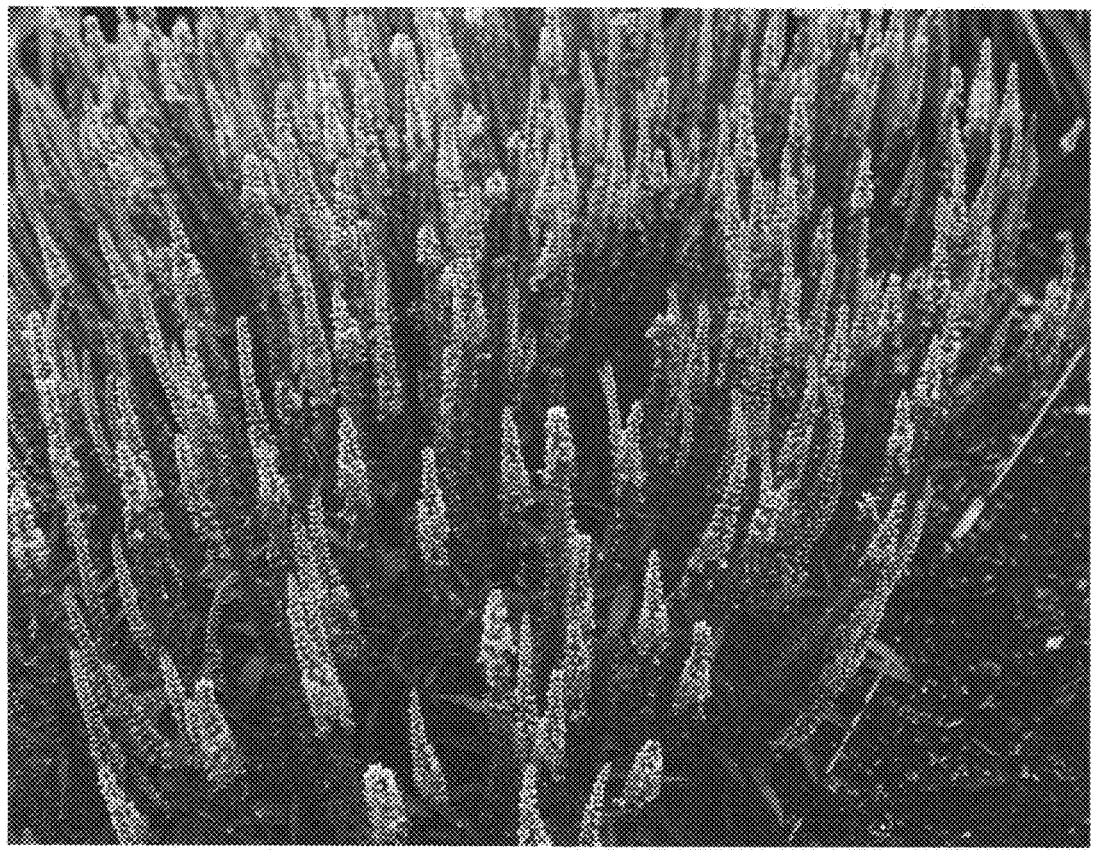
FIG. 2 shows the plant in full flower.

The following descriptions and color references are based on the 2001 edition of The Royal Horticultural Society Colour Chart except where common dictionary terms are used. *Veronica spicata* 'Foxy Lady' has not been observed under all possible environments. The phenotype may vary slightly with different growing environments such as temperature, light, fertility, soil pH, moisture and maturity levels, but without any change in the genotype. The following observations and size descriptions are based on two-year old plants in the full sun trial garden of a nursery in Zeeland, Mich. with supplemental fertilizer and water as needed.

Botanical classification: *Veronica spicata;*

Parentage: Uninduced whole-plant sport of *Veronica spicata* 'Red Fox' (not patented);

Plant habit: Hardy herbaceous perennial, compact, with several stems, 10 to 12 cm tall without scapes and 35 to 40 cm wide; flowering beginning late June in Mich. and continuing for about 6 weeks with occasional repeat if deadheaded;

Leaves: Simple, lanceolate, opposite, serrated, minutely pubescent below and above, acute apex, attenuate base; 4 to 6 cm long by 1.5 to 2.2 cm wide, RHS 137C on top, RHS 138C below;

Veins: Minutely pubescent below and above, arcuate, same color ( RHS 137C) as leaf on adaxial surface; center vein and secondary veins closest to center vein on abaxial surface RHS 141D; main vein about 0.5 mm diameter;

Petiole: 2.5 to 3.0 cm long and 2 mm wide; RHS 144C nearest stem and RHS 137C nearest blade;

Buds two days prior to opening: Convolute, narrowly oblong, obtuse apex; about 4 mm long and 1.5 mm diameter; appearing almost longitudinally striped with RHS 64B and white with no visible tinting pigment;

Flowers: On seldom branched upright spike; numerous, approximately 200; 8 mm in diameter and about 7 mm deep; no detectible fragrance; flowers persist individually for 3 to 5 days whether on the plant or cut, self-cleaning;

Petals: Four, simple, entire, with rounded apex and fused at base, 5 mm long by 3 mm wide, glabrous outer and inner sides except with 2 mm long hairs of RHS 62D at inside base;

Petal color: Identical on inner and outer sides, central petal portions darkest ruby between RHS 64A and 64B, lightening to RHS 61C before the margin edge of whiter than RHS 69A or N155B; margin width is feathered and irregular;

Filaments: Two, 5 mm by 0.25 mm, between RHS 73B and RHS 73C;

Anther: Elliptic, 1.5 mm by 1.0 mm, RHS 59A;

Pollen: Abundant, globose, less than 0.1 mm; RHS 11C;

Style: 4.0 mm by 0.25 mm, RHS 64A;

Stigma: Cylindrical, 0.25 mm in diameter; persists after petals drop; RHS 59B;

Ovary: 1.0 mm by 0.75 mm, between RHS 143D and RHS 144B;

Sepals: Four, acute apex, base fused forming corolla, with minute hairs on margin and sparsely pubescent on the outer surface, lowest one 4 mm long by about 0.5 mm wide, other three 3 mm long by about 0.5 mm wide, RHS 137A both surfaces;

Peduncle: About 20 per plant; raceme, strong, erect, round, pubescent; about 25 cm long and 3 mm in diameter at base, flowering section of the main stem about 18 cm long, occasionally with two opposite branches of 15 to 20 cm long and flowering on the terminal 10 to 17 cm; with less frequent branching at the lower nodes about 5 to 7 cm with flowering in the terminal 2 to 3 cm; color nearest RHS N144A with some anthocyanin tinting of RHS 59A; diameter of flowering portion of raceme about 2 cm;

Pedicel: Upright, rigid, sparsely pubescent with minute hairs, subtended by minutely pubescent bract of about 3 mm long and 1.0 mm wide, bract RHS 137A both surfaces; pedicel 1.0 to 3 mm long and less than 1.0 mm in diameter; nearest RHS 138B;

Fruit: Elliptic, less than 1 mm long; between RHS 166A and RHS 166B;

Hardiness, pest and disease resistance: The plant grows best with plenty of moisture and adequate drainage, but is able to tolerate some drought when mature. Hardiness at least from USDA zone 4 through 8. Disease and pest resistance beyond what is typical of that of other Spiked Speedwell has not been observed.

I claim:

1. A new and distinct cultivar of ornamental Spiked Speedwell, *Veronica spicata* 'Foxy Lady', as herein described and illustrated, with erect compact spikes of numerous two-tone ruby and white buds and flowers above low mats of foliage and suitable as a potted plant, for the garden, and for cut flower arrangements.

* * * * *